United States Patent [19]

Mandl

[11] Patent Number: 4,551,136
[45] Date of Patent: Nov. 5, 1985

[54] PRESSURE INFUSOR
[75] Inventor: Joseph P. Mandl, Lancaster, Ohio
[73] Assignee: Medex, Inc., Hilliard, Ohio
[21] Appl. No.: 483,767
[22] Filed: Apr. 11, 1983
[51] Int. Cl.$^4$ .................................. A61M 5/00
[52] U.S. Cl. .................................. 604/141; 222/95
[58] Field of Search .................. 604/140–145; 222/92, 95, 105

[56] References Cited

U.S. PATENT DOCUMENTS

| 2,766,907 | 10/1956 | Wallace | 604/141 X |
| 3,153,414 | 10/1964 | Beall et al. | 604/141 X |
| 3,603,304 | 9/1971 | Maier | 128/686 |
| 3,765,405 | 10/1973 | Natkanski | 128/686 |
| 4,090,514 | 5/1978 | Hinck et al. | 604/142 |

Primary Examiner—Dalton L. Truluck
Attorney, Agent, or Firm—Wood, Herron & Evans

[57] ABSTRACT

A pressure infusor for introduction of fluids into the human body. Two sheets of polyurethane overlie each other and are continuously sealed to form an air-inflatable bladder. A strip of polyurethane projects from one vertical margin of the bladder to wrap completely around the liquid-filled bag. A narrow elongated strap is centrally attached to one margin of the infusor and is long enough to wrap completely about the infusor with a bag enclosed. Velcro strips are secured to the strap so that it can be fastened upon itself.

2 Claims, 4 Drawing Figures

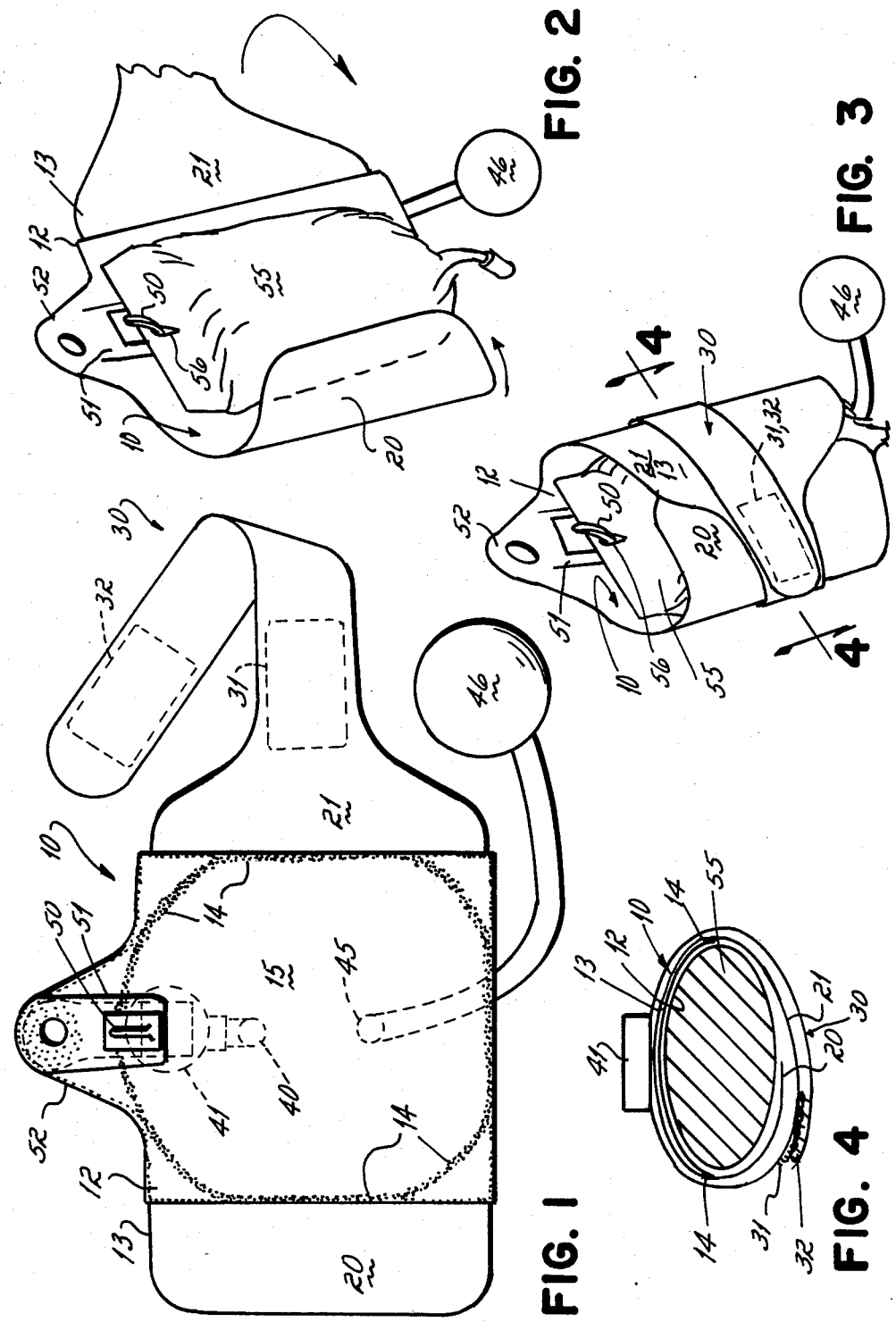

PRESSURE INFUSOR

This invention relates to a pressure infusor, that is, an air-inflatable bladder adapted to be wrapped about a fluid-filled bag and inflated in order to raise the pressure in the bag to the level of 300 mm Hg, for example.

The function of the infusor is to drive fluids into the human body. For example, blood is quite viscous, especially when it has been refrigerated, and requires pressure to drive it rapidly into the circulatory system of the patient when that patient is rapidly losing blood. A pressure infusor is needed for the rapid infusion of an intravenous solution. When the pressure is raised to 300 mm $H_g$, the rapidity of the infusion increases three or four-fold as contrasted to gravity. In invasive blood pressure applications, constant pressurization of the fluid container is needed to continuously drive the fluid toward the patient through flush devices.

One highly successful pressure infusor consists of a two-layer cloth sleeve containing a separate polyurethane bladder within the sleeve. A filled bag such as an I.V. bag is pulled through the sleeve (a two-handed operation) and is connected to the sleeve so that the sleeve and bag may be mounted on an I.V. pole. This device has its disadvantages. It is opaque and as a consequence the attendant cannot easily determine either the quantity of fluid remaining in the bag or the quality, that is, whether it is a blood or saline solution. As suggested, it is a somewhat time-consuming, two handed operation to insert the bag in the sleeve and hang it. This might be particularly disadvantageous, for example, when an anesthesiologist is on the one hand pumping oxygen into the patient and on the other hand monitoring a blood transfusion of I.V. infusion. In such a situation, time could be of the essence when a new bag has to be applied.

Hinck attempted a solution to the problem as disclosed in U.S. Pat. No. 4,090,514. That pressure infusor consists of a vinyl laminate having a continuous seal to form a bladder 15. The laminate has marginal portions to which vertical Velcro strips are applied to fasten the ends of the bladder around a bag.

The pressure infusor of that patent has had two significant problems: First, the Velcro fastener tended to pop apart, with a somewhat alarming pop, as high pressure was introduced into the bladder. Second, leakages occurred in the bladder seals. One attempt to solve the problem of leakage was to introduce a separate bladder into a compartment formed by making the continuous seal around the laminate, but even that improvment did not satisfy the need for a substantially leak-proof bladder.

An objective of the present invention has been to provide a transparent pressure infusor which has the following attributes: it is leak-proof under the pressures normally applied during infusion procedures, it is easily cleaned, it is easily and efficiently handled by the attendant, but will apply substantially uniform pressure along the height of the bag and it will stay securely wrapped about the bag.

This objective of the invention is attained by forming a bladder from two sheets of transparent polyurethane, the sheets overlying one another and having a continuous seal to form the bladder. An elongated narrow strap, which may be integral with one of the sheets or separately sealed to it, is connected to one vertical margin of the bladder and is adapted to be completely wrapped around the bladder when a bag is contained within the bladder.

A conventional bag contains 500 cc of fluid. The bag is about 10 inches in circumference and 7 inches in height. In accordance with the present invention, the bladder has a length of about 8 inches and is about 8 inches in height. In order to provide a complete wrap around the bag, including overlying marginal portions, a marginal, vertically-extending strip projects from at least one margin of the bladder a sufficient distance to provide about a 2 inch overlap when the bladder and marginal strip is wrapped around a bag.

The coefficient friction of the polyurethane with respect to itself is quite high. Therefore, the overlap of polyurethane upon itself tends to keep the pressure infursor from coming apart and tends to maintain a uniform pressure on the bag around the height of the bag. The elongated strap which is wrapped and Velcro-secured upon itself keeps the overlapping portions of the bag in contact so that the frictional resistance to separation is maintained. Further, the orientation of the two Velcro strips (hook and loop) permits them to remain securely fastened together even under the high infusion pressures applied to the bag. There is thus a synergistic relationship between the strap forming a fastening around the bag which applies a force to the overlapping marginal portions of the bag to increase their resistance to separation.

The bladder has two vertically-spaced ports, one being an air inlet port and one being a port connected to a gauge so that the pressure of the bladder can be directly read. These ports are spaced apart a sufficient distance so that the narrow strap can fit between them. Finally, the bladder has an internal hook from which a bag can be hung to center it on the bladder, and it has an eyelet for mounting it upon an I.V. pole.

As suggested above, the resultant bag is clear so that the volume and quality of the contents can be ascertained. It is cleanable, easy to handle, efficient, leak-proof and will not inadvertently pop open.

In use, a depleted bag can be removed as a one-handed operation simply by jerking open the Velcro fastener and permitting the bladder to unwrap. The depleted bag can then be lifted off its hook and a full bag applied. Thereafter, two hands are normally required to wrap the bladder about a fresh bag of liquid and then the strap around the bladder and to reconnect the bag to the patient's administration system.

The several features and objectives of the present invention will become more readily apparent from the following detailed description taken in conjunction with the accompanying drawings in which:

FIG. 1 is a plan view of the bladder of the present invention in an unwrapped condition;

FIG. 2 is a perspective view showing the bladder partially wrapped about a bag;

FIG. 3 is a perspective view showing the bladder fully wrapped about the bag;

FIG. 4 is a highly schematic cross-sectional view taken along lines 4—4 of FIG. 3.

The pressure infusor of the present invention is shown at 10 in FIG. 1. It includes two transparent polyurethane sheets 12 and 13 overlying one another. The sheets are each about 0.035 inch thick. A continuous seal 14 is formed between the sheets around the perimeter of them to form a pressure-tight bladder 15. The bladder has a dimension of approximately 8 inches in the vertical direction and approximately 8 inches in the horizontal direction. Along one margin (the left as viewed in FIG. 1), a vertical strip 20 extends. That strip is approximately 2.5 inches wide and extends the full height of the bladder.

Along the opposite margin, a strip 21 of 2.5 to 3 inches extends substantially the height of the bladder. When the bladder is applied, a substantial portion of the strips 20 and 21 will overlap each other, and through the friction of the two surfaces will tend to resist opening.

An elongated strap 30 about 2 inches wide is formed integrally with the strip 21. It has a Velcro loop strip 31 and a Velcro hook strip 32 secured to the strap. The distance between the strips 31 and 32 is sufficient to enable the strap to be wrapped completely about the bladder and contents with the Velcro strips overlapping in attaching engagement.

It should be understood that the strip 21 could be eliminated and the strap 30 connected directly to the sheet 13. In his case, the strip 20 should be widened by approximately 3 inches so that it can be wrapped around the bag and have at least about a 2 inch overlap with the bladder. At the upper portion of the bladder 15, a gauge port 40 is formed in the sheet 13. A gauge 41 is attached to the port and is preferably secured to the surface of the bladder on the outside thereof by means of matching Velcro strips secured respectively to the bladder and the gauge.

Spaced about 2.5 inches below the gauge port is an inlet port 45 to which a squeeze bulb 46 is attached for inflating the bladder. A hook 50 is secured to a strap 51, the strap being sealed to a mounting flap 52 on the bladder. The hook provides a place to mount the bag 55 of liquid to be wrapped in the bladder and pressurized. The bag has an eyelet 56 at one end by means of which the bag is conveniently mounted on the hook.

The bag is about 10 inches in circumference and 7 inches height. The inflatable portion of the bladder has a length of about 8 inches and a height of about 8 inches. The marginal strip 20 is about 2.5 inches and the marginal strip 21 is about 3 inches wide. The length of the strap 30 extending beyond the marginal strip 21 is about 14 inches long.

In operation, the bladder is hung on an I. V. pole and a bag 55 is hung on the hook 50. The bladder is wrapped about the bag with the marginal strip 20 overlying the bag and the strip 21 overlying the strip 20 so that friction between the overlying surfaces of strips 20 and 21 tends to hold the strips together. The strap 30 is then wrapped around the bladder and a Velcro strip 32 is applied with pressure to Velcro strip 21 to securely attach the overlying portions of the strap 30.

Air is pumped into the bladder by means of the bulb 46 until the gauge indicates that the desired pressure has been attained. As presssure is applied to the bladder, it expands and presses strip 20 against strip 21. The frictional resistance to separation is increased as the pressure in the bladder is increased. When the desired pressure is attained, the administration set, previously applied to the bag, is then in condition to introduce fluid into the patient under the pressure provided by the inflated bladder acting upon the bag.

Having described my invention, I claim:

1. A pressure infusor comprising,
    a transparent polyurethane outer sheet approximately 0.035 inch thick,
    a transparent polyurethane inner sheet approximately 0.035 inch thick and overlying said outer sheet with approximately a 2.5 inch margin of said outer sheet projecting beyond said inner sheet at opposed edges thereof,
    a continuous seal around the coextensive portions of said sheets to form a closed pressure bladder,
    said 2.5 inch margins extending along said entire edges of said bladder,
    one of said margins at least partially overlying the other margin when said outer sheet is wrapped around a fluid-containing plastic bag, said polyurethane margins having a high coefficient of friction when in said overlying relation, thereby resisting opening said outer sheet,
    an elongated narrow strap projecting approximately 17 inches from one of the margins,
    said strap totally surrounding said pressure bladder and fluid-containing bag and overlying said margins when said outer sheet is wrapped around a plastic fluid-containing bag,
    said strap having cooperating Velcro fastening strips secured thereto to fasten said strap around said bag,
    means for applying fluid under pressure to said bladder and means for measuring said pressure.

2. A pressure infusor comprising,
    a transparent polyurethane outer sheet,
    a transparent polyurethane inner sheet overlying said outer sheet with approximately a 2.5 inch margin of said outer sheet projecting beyond said inner sheet at opposed edges thereof,
    a continuous seal around the coextensive portions of said sheets to form a closed pressure bladder,
    said margins extending along said entire edges of said bladder,
    one of said margins at least partially overlying the other margin when said outer sheet is wrapped around a fluid-containing plastic bag, said polyurethane margins having a high coefficient of friction when in said overlying relation, thereby resisting opening said outer sheet,
    an elongated narrow strap projecting from one of the margins,
    said strap totally surrounding said pressure bladder and fluid-containing bag and overlying said margins when said outer sheet is wrapped around a plastic fluid-containing bag,
    said strap having cooperating Velcro fastening strips secured thereto to fasten said strap around said bag,
    means for applying fluid under pressure to said bladder and means for measuring said pressure.

\* \* \* \* \*